US007456752B2

(12) United States Patent  
Oberle

(10) Patent No.: US 7,456,752 B2  
(45) Date of Patent: Nov. 25, 2008

(54) RADIO FREQUENCY IDENTIFICATION SENSOR FOR FLUID LEVEL

(75) Inventor: Robert R. Oberle, East Winsor, NJ (US)

(73) Assignee: RCD Technology, Inc., Quakertown, PA (US)

( * ) Notice: Subject to any disclaimer, the term of this patent is extended or adjusted under 35 U.S.C. 154(b) by 0 days.

(21) Appl. No.: 10/839,012

(22) Filed: May 5, 2004

(65) Prior Publication Data

US 2005/0017727 A1    Jan. 27, 2005

Related U.S. Application Data

(60) Provisional application No. 60/458,130, filed on May 6, 2003.

(51) Int. Cl.
*G08B 21/00* (2006.01)
(52) U.S. Cl. .......... 340/604; 340/603; 340/572.8; 340/539.26; 73/304 C; 73/304 R
(58) Field of Classification Search ........... 340/604, 340/870.16, 539, 572.8, 539.26, 539.28, 340/618, 620, 602; 73/304 C, 304 R, 53.01, 73/61.58, 61.41–43, 61.68; 210/602, 86, 210/85; 137/392
See application file for complete search history.

(56) References Cited

U.S. PATENT DOCUMENTS 3,759,246 A * 9/1973 Flack et al. ............... 600/573
5,058,161 A    10/1991 Weiss
5,463,377 A *  10/1995 Kronberg .................. 340/605
5,598,032 A    1/1997 Fidalgo
5,629,981 A    5/1997 Nerlikar
5,874,902 A    2/1999 Heinrich et al.
5,892,611 A    4/1999 Iisuka
5,942,978 A    8/1999 Shafer
5,963,134 A    10/1999 Bowers et al.
6,049,461 A    4/2000 Haghiri-Tehrani et al.
6,089,284 A    7/2000 Kaehler et al.
6,111,520 A *  8/2000 Allen et al. ............ 340/870.16
6,133,833 A    10/2000 Sidlauskas et al.
6,204,760 B1   3/2001 Brunius
6,268,796 B1 * 7/2001 Gnadinger et al. ....... 340/572.5
6,400,323 B2   6/2002 Yasukawa et al.
6,421,013 B1   7/2002 Chung
6,514,790 B1   2/2003 Plettner et al.
6,774,800 B2 * 8/2004 Friedman et al. ......... 340/573.5
6,849,936 B1   2/2005 Berman et al.
2002/0140608 A1  10/2002 Zaghloul et al.
2003/0116790 A1  6/2003 Kikuchi et al.
2004/0070510 A1 * 4/2004 Zhang et al. .............. 340/618
2004/0203235 A1  10/2004 Miyakawa

FOREIGN PATENT DOCUMENTS

EP    0 903 805 A2    3/1999

* cited by examiner

*Primary Examiner*—George A Bugg
*Assistant Examiner*—Travis Hunnings
(74) *Attorney, Agent, or Firm*—Fliesler Meyer LLP

(57) ABSTRACT

A sensor can detect the presence of fluid by the changing of the response characteristics of an RLC circuit. A window in the sensor is used to position a short caused by the fluid.

18 Claims, 5 Drawing Sheets

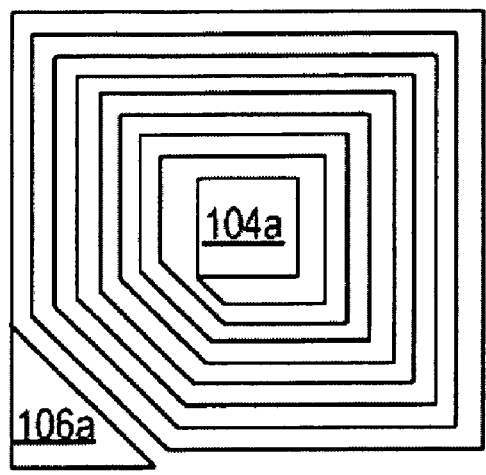
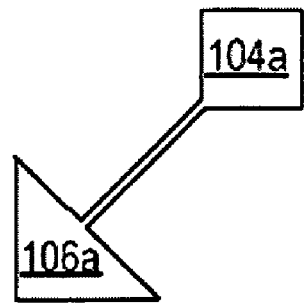
FIG. 1A
PRIOR ART
FIG. 1B
PRIOR ART
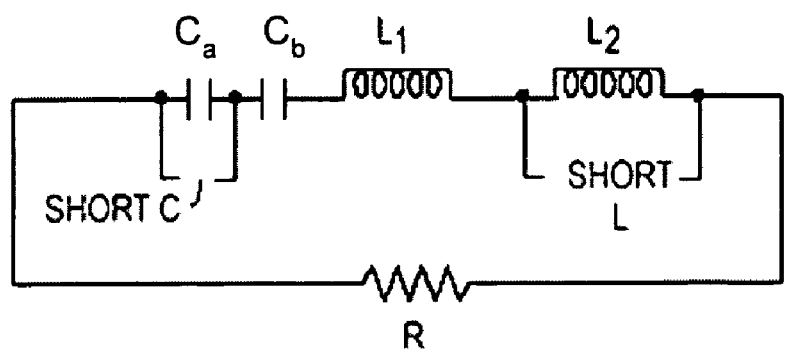
FIG. 2

RADIO FREQUENCY IDENTIFICATION SENSOR FOR FLUID LEVEL

CLAIM OF PRIORITY

This application claims priority to U.S. Provisional application 60/458,130 filed May 6, 2003, which is incorporated herein by reference.

BACKGROUND OF INVENTION

Passive Radio Frequency ID (RFID) devices are broadly defined as radio frequency transponders that are activated and powered by the RF field of a remote detector or reader. Common examples are electronic anti-shoplifting (EAS) tags sold by Checkpoint Systems of Thorofare, N.J. An EAS tag is affixed to a retail item and the movement of the item into the field of the RF detector may be sensed by the absorption of RF energy by the resonant circuit in the tag. In more advanced systems a small integrated circuit (IC) may be incorporated into the circuit. This IC is powered by the remote RF field and may respond to the field by broadcasting data that may be interpreted by the reader. The data may be a unique serial number to identify the item or a more complex data set. There are a number of such commercial systems available for tracking and inventory applications.

FIG. 1A-1B show the conductive layers for a prior art radio frequency sensor. FIG. 1A shows a top conductive layer. This top conductive layer is positioned over a substrate. FIG. 1B shows the bottom conductive layer. The top layer shows the conductive coil 102 and the top plates 104A and 106A of capacitor regions. These capacitor regions also include the bottom plates 104B and 106B shown in FIG. 1B and the intervening substrate.

BRIEF DESCRIPTION OF THE DRAWINGS

FIGS. 1A and 1B illustrate the top and bottom conductive layers of a prior art RFID tag.

FIG. 2 illustrates an embodiment of the present invention.

DETAILED DESCRIPTION

Figure 5A:
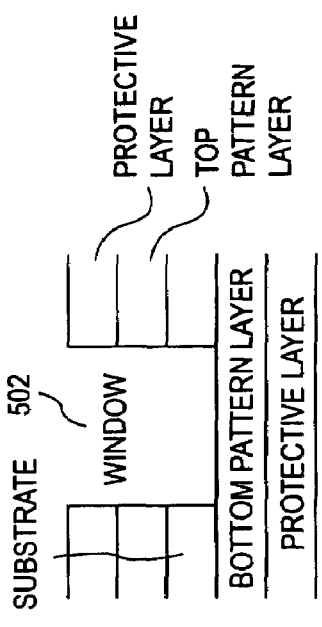
FIG. 5A illustrates a cross-section of a sensor of an embodiment of the present invention.

One purpose of the proposed invention is to provide for fluid detection through the use of RFID detection technology. In the invention and RFID circuit responds to the presence of a fluid and is able to communicate the detection to another system via a change in response to query by an electromagnetic field of a passive circuit. The passive circuit need not be physically connected to the sensing instrumentation that makes the query, nor is it necessary that the circuit be physically connected to an electrical power source. It is envisioned that the fluid to which the circuit responds may be either liquid or vapor, thought for purposes of explanation a liquid fluid is used in the following illustrations. It is also assumed that the circuit may respond to one or more components in the fluid i.e. a minority constituent in the fluid matrix may elicit a response in the circuit.

In order to detect the presence of a fluid, the electrical response of the RFID circuit must change in the presence of the fluid. This change in response may be manifest in a change of resonant frequency of an RLC circuit (an RLC circuit contains a combination of passive electrical components resistance, capacitance and inductance). The resonant frequency may be changed by a changing the value of the inductance of the capacitance of the circuit as may be seen from the expression for resonant frequency:

$$f = \frac{1}{2\pi}\sqrt{\frac{1}{LC}}$$

, where f is the frequency in Hertz, L is the inductance in Henrys and C is the capacitance in Farads. Two simple examples of a short in an RLC includes one which changes the capacitance, C, and the second which changes the inductance, L. In either case the short may be accomplished by introduction into the circuit into a fluid which is electrically conductive e.g. salt water, urine, electroplating solution etc. In another manifestation the short may be accomplished by activation of a conductive path by a component in the fluid e.g. a salt bridge which becomes conductive in the presence of water vapor. In yet another manifestation the conductive path may be activated by dissolution of an insulating component by the fluid or chemical reaction with a specific component in the fluid e.g. activation of a conductive trace by a specific chemical reaction. By the use of appropriate chemical markers the resonant circuit could be specific to a specific chemical or component. An array of resonant circuits could be used as a screening tool for numerous components in a fluid.

Another advantage of the configuration shown below is that the presence of the circuit in the field can be verified and the state of activation of the circuit can be verified by a shift of the resonant frequency, or system inductance.

The present invention may be realized in a number of configurations, a simple illustration is shown in FIG. 2 but others may be envisioned by those skilled in the art. In FIG. 2 the substrate is a nonconductive film, such as polyester, which forms the dielectric layer for capacitors $C_a$ and $C_b$. The coil serves as the source of inductance in the circuit and the internal resistance of the coil determines the quality factor of the circuit, Q. When the circuit is immersed in a fluid electrolyte the capacitor $C_b$ is shorted and the resonant frequency shifts from $f_{ab}$ to $f_a$. Either short C or Short L or both together may be used to shift the frequency of the circuit. The backside of the substrate film can be metalzed and the circuit can be covered with an insulator (protective layer) except in the vicinity of window.

One embodiment of the present invention is a sensor that modifies its behavior in the presence of a fluid. The sensor can include a substrate, which can be a non-porous substrate. A tuned RLC circuit can be configured on the substrate. The tuned RLC circuit can include an inductor coil and a capacitor coupled through said substrate. A film can be configured to limit exposure of the inductor coil to fluid. The film can have one or more windows positioned such that fluid exposure is defined by the one or more windows. The fluid introduced through the one or more windows can cause a short in the RLC circuit.

Fluid introduced at the one or more windows can produce an electrical short across two or more turns of the inductor coil. Alternately, fluid at the one or more windows can produce a short at the capacitor.

Exposure to the fluid can be determined by measuring the change in resonant frequency of the tuned RLC circuit during exposure to an electrically conductive fluid though the window in the film. Exposure to the fluid can be determined by measuring the change in impedance of the RLC circuit before and after exposure to an electrically conductive fluid.

The RLC circuit can be initially tuned to a frequency between 6 MHz and 25 MHz.

The window can be positioned such that the fluid exposure causes a predictable change in electrical impedance and/or resonant frequency of the circuit.

An exposure to an electrically conductive fluid can cause a shift in resonant frequency through a change in resonant frequency, capacitance, inductance or resistance of the circuit.

Figure 4A:
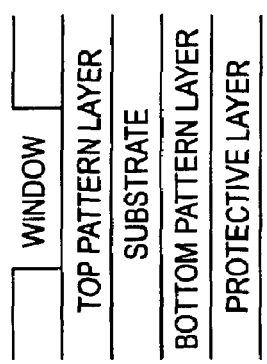
FIG. 4A illustrates a cross-section of a sensor of one embodiment of the present invention.
Figure 3A:
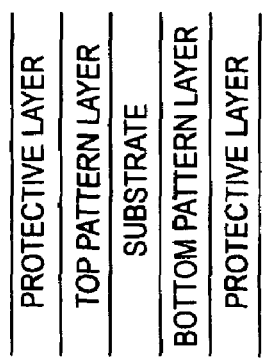
FIG. 3A illustrates a cross-section of a conventional RFID tag.
Figure 3B:
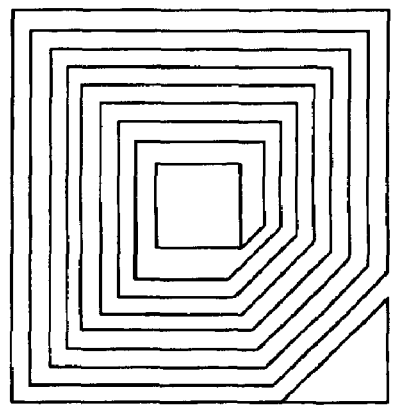
FIG. 3B illustrates a top conductive layer corresponding to the RFID tag of FIG. 3A.

FIGS. 3-5 illustrate the use of the windows to change the property of the sensor. FIGS. 3A and 3B show conventional tags. FIG. 3A shows a cross-section of the layers. FIG. 3A shows a protective layer, a top pattern layer, a substrate layer, a bottom layer and another protective layer. FIG. 3B illustrates a top conductive layer corresponding to the sensor of FIG. 3A.

Figure 4B:
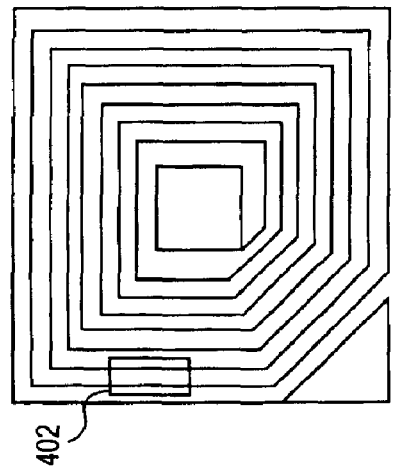
FIG. 4B illustrates a top conductive layer corresponding to the sensor of FIG. 4A with a window positioned over turns of a coil of the RFID tag.

FIG. 4 shows an embodiment with a window 402 positioned to expose the top pattern layer to a fluid. As shown in FIG. 4B this window exposure can between one or more turns of the conductive coil as shown in FIG. 4B with the window 402. The window can be filled with material that becomes conductive when contacting with the fluid, such as water, or can be open to the environment such that any electrically conductive fluid, such as urine, will cause a short between the turns of the coil. Such a short will change the characteristics of the RLC circuit.

Figure 5B:
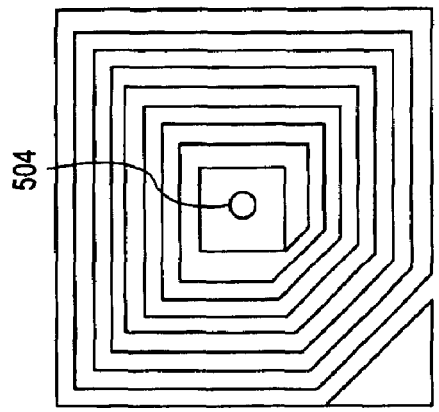
FIG. 5B illustrates a top conductive layer corresponding to the sensor of FIG. 5A with a window positioned through a capacitor region of the sensor.

FIG. 5A-5B illustrates an example where the window is used such that the fluid causes a short of the capacitor. FIG. 5A shows a window 502 which extends through the protective layer down through the substrate to the bottom pattern layer. In this example, the fluid entering the window 502 of FIG. 5A will produce a short between the top and bottom conductive plates. FIG. 5B shows the window 504 in the capacitor.

In one embodiment, the presence of the fluid modifies the response characteristics of the RLC circuit such that the fluid sensor can be used in a three state system where the fluid sensor in the presence of fluid has a different response characteristic from a missing fluid sensor. Such a three state system is an improvement on systems that cannot distinguish between the presence of fluid and the absence of the sensor.

Figure 6:
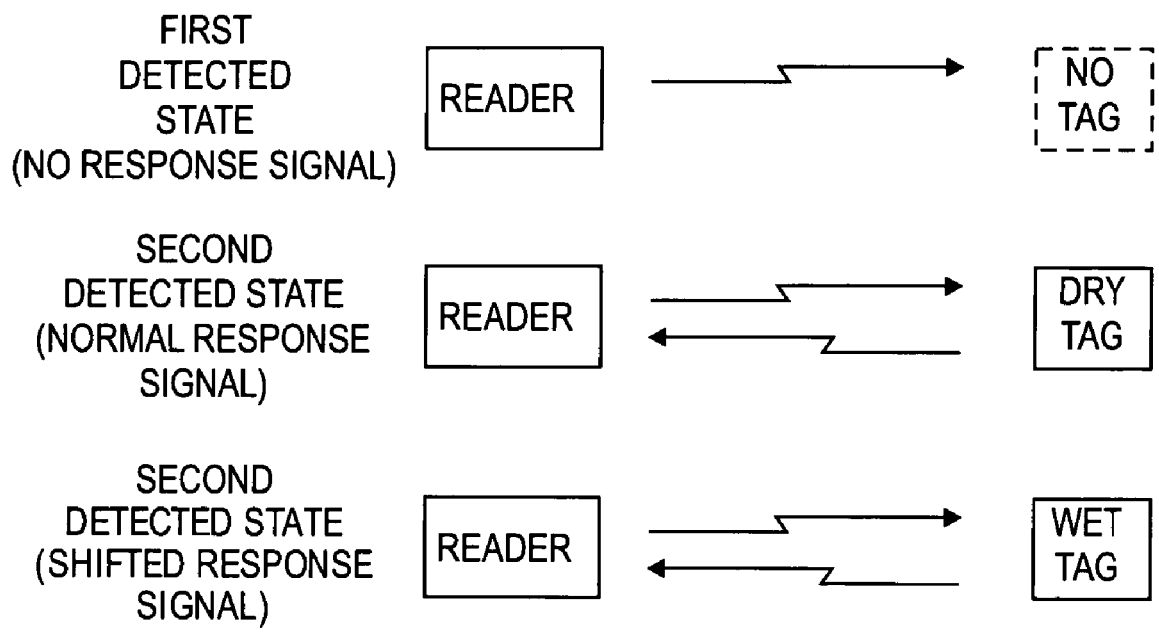
FIG. 6 illustrates a three state system using a sensor of the present invention.

FIG. 6 illustrates the three state nature of the system. The first detectable state is the no response signal. This corresponds to the situation where the tag or sensor is not present. The second detected state is the normal response signal in which the tag or sensor is dry or otherwise not effective by the fluid and the normal response signal occurs. The third detected state is the modified response signal caused by the wet (or otherwise affected by the fluid) tag or sensor. By being able to distinguish between the first and third state the system has advantages for operation with units where a sensor is not sure to be present. Additionally, the three state system has the benefit of allowing the user to be able to adjust the reader or detector until a response signal is found and from the detected signal determine whether fluid is present.

The one or more windows can be covered or include a material that becomes conductive upon exposure to a fluid containing a specific component or class of components. In one embodiment, there are multiple windows at least two of are independently covered with differing receptive/reactive compounds that become conductive in response to exposure to differing components of the fluid.

Figure 7:
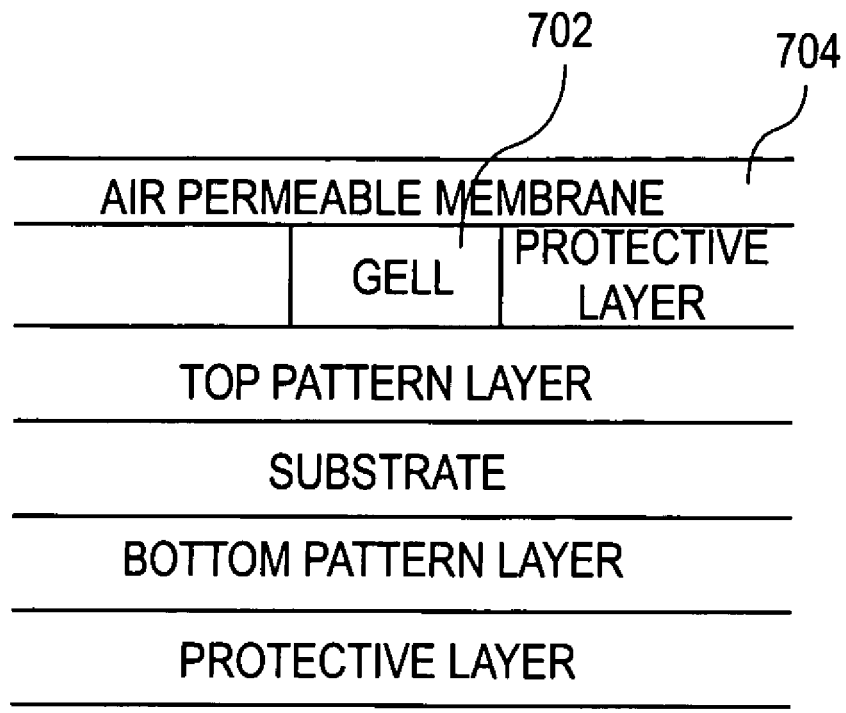
FIG. 7 illustrates a cross-section of a sensor using a gel of one embodiment of the present invention.
Figure 8:
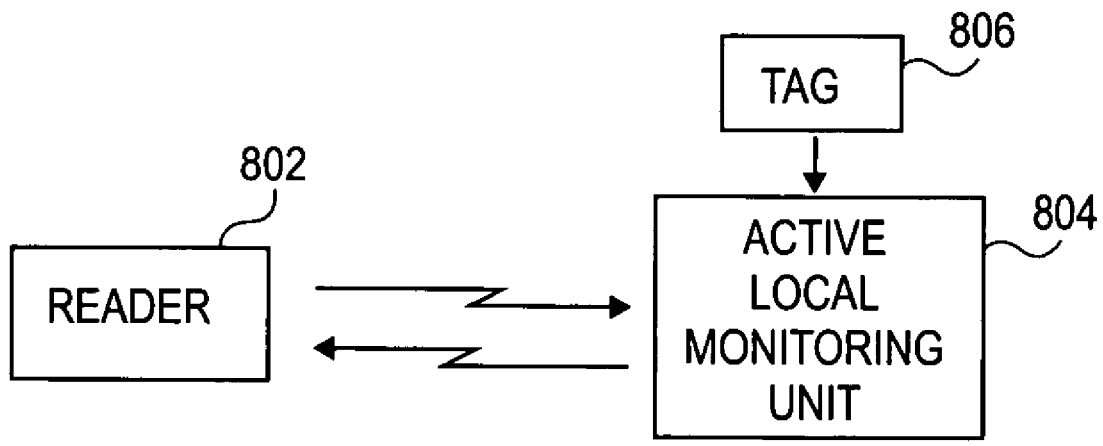
FIG. 8 illustrates the use of the sensor with an active local monitoring unit.

FIG. 7 show an embodiment where the window is filled with a gel. The gel can be protected by an air permeable membrane 704. In this embodiment, the gel can contain a material that can reacts with specific gas such that gel becomes conductive and changes the characteristics of the sensor. For example, the gel can contains a compound that reacts with nerve gas to produce Floride ions in the gel. The Floride ions can make the gel conductive and thus cause the sensor to change in its characteristics.

FIG. 7 show an embodiment where the window is filled with a gel 702. The gel 702 can be protected by an air permeable membrane 704. In this embodiment, the gel can contain a material that can reacts with specific gas such that gel becomes conductive and changes the characteristics of the sensor. For example, the gel 702 can contains a compound that reacts with nerve gas to produce Floride ions in the gel. The Floride ions can make the gel conductive and thus cause the sensor to change in its characteristics.

Figure 9:
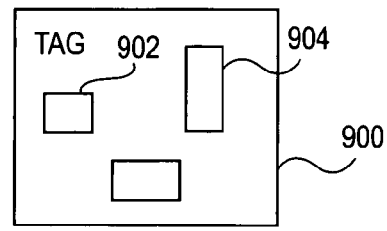
FIG. 9 illustrates an example where the fluid sensor has multiple windows

FIG. 9 illustrates an example where the fluid sensor has multiple windows. The windows can contain different materials such that the sensor 900 can detect different fluids or fluid components. In one embodiment, a short in window 902 produces a different change in the response characteristics of the RLC circuit than a short in window 904, so the type of fluid can be determined.

Figure 10A:
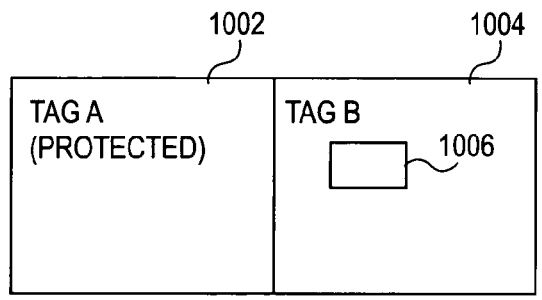
FIG. 10A-10C illustrate an embodiment where the fluid sensor can have multiple RLC circuits.
Figure 10B:
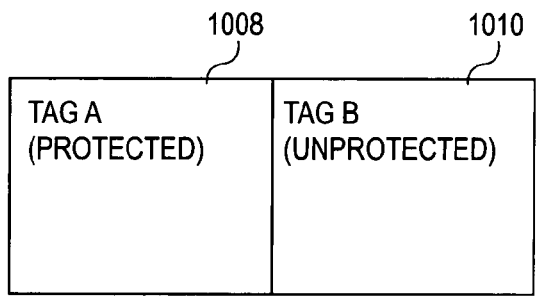
Figure 10C:
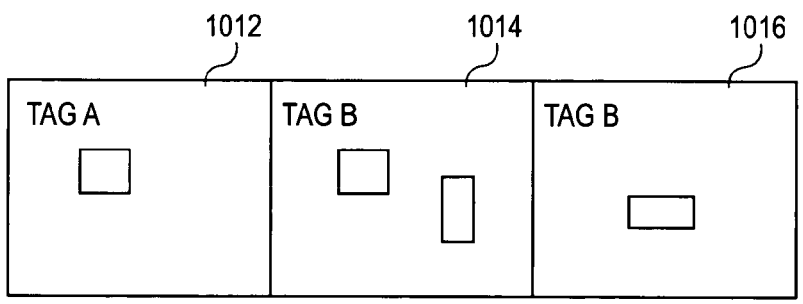

FIG. 10A-10C illustrate an embodiment where the fluid sensor can have multiple RLC circuits. The RLC circuits can be tuned to the same or different frequencies. In one embodiment, the first and second tuned RLC circuits are formed on at least one substrate. The RLC circuits can be formed on a single or separate substrates. The RLC circuits can be connected together (such as adjacent to one another) or separate (such as positioned in the same container or diaper). The tuned RLC circuits include inductor coils and capacitors coupled through said at least one substrate. The first and second tuned RLC circuits cam have different responses to the introduction of fluid. At least one of the first and second tuned RLC circuits changes its response characteristics with the introduction of a fluid at the fluid sensor.

FIG. 10A illustrates an example where RLC circuit 1002 is protected from fluid so that its response characteristics does not change with the introduction of a fluid at the fluid sensor. The RLC circuit 1004 has a film configured to limit exposure of the inductor coil to fluid, the film having one or more windows 1006 positioned such that fluid exposure is defined by the one or more windows 1006, wherein fluid introduced through the one or more windows 1006 can cause a short in the RLC circuit.

FIG. 10B illustrates an example where RLC circuit 1008 is protected from fluid so that its response characteristics does not change with the introduction of a fluid at the fluid sensor. RLC circuit 1010 is unprotected from fluid.

FIG. 10C illustrate a case where multiple RLC circuits 1012, 1014 and 1016 have windows. The window patterns can be the same or different for each RLC circuit. Protected and unprotected RLC circuits can be also used.

The sensor can also be considered to be an environmental sensor since the environmental elements such as a fluid including liquid or gas can be detected by the change in characteristic of the RLC circuit.

Systems of the present invention can be used for detecting fluid in a wide range of the systems. For example, the system can be used to detect urine in diapers to determining when a user should replace a diaper.

The foregoing description of preferred embodiments of the present invention has been provided for the purposes of illustration and description. It is not intended to be exhaustive or to limit the invention to the precise forms disclosed. Many embodiments were chosen and described in order to best explain the principles of the invention and its practical application, thereby enabling others skilled in the art to understand the invention for various embodiments and with various modifications that are suited to the particular use contemplated. It is intended that the scope of the invention be defined by the claims and their equivalents.

What is claimed is:

1. A fluid sensor comprising:
   a substrate; and
   a tuned RLC circuit configured on the substrate, the tuned RLC circuit including an inductor coil and a capacitor coupled through said substrate, and
   a film configured to limit exposure of the inductor coil to fluid, the film having one or more windows positioned such that fluid exposure is defined by the one or more windows, wherein fluid introduced through the one or more windows can cause a short in the RLC circuit; wherein an exposure to an electrically conductive fluid causes a shift in resonant frequency form a first to a second non-zero frequency through a change in inductance of the circuit;
   wherein the one or more windows in the film is covered with a material that becomes conductive upon exposure to a fluid containing a specific component or class of components and;
   wherein there are multiple windows at least two of which are independently covered with differing receptive/reactive compounds that become conductive in response to exposure to differing components of the fluid.

2. A fluid sensor comprising:
   a substrate; and
   a tuned RLC circuit configured on the substrate, the tuned RLC circuit including an inductor coil and a capacitor coupled through said substrate, and
   a film configured to limit exposure of the inductor coil to fluid, the film having one or more windows positioned such that fluid exposure is defined by the one or more windows, wherein fluid introduced through the one or more windows can cause a short in the RLC circuit;
   wherein the presence of the fluid modifies the response characteristics of the RLC circuit such that the fluid sensor can be used in a three state system where the fluid sensor in the presence of fluid has a different response characteristic from an absent fluid sensor; wherein an exposure to an electrically conductive fluid causes a shift in resonant frequency through changing inductance;
   wherein the one or more windows in the film is covered with a material that becomes conductive upon exposure to a fluid containing a specific component or class of components and;
   wherein there are multiple windows at least two of which are independently covered with differing receptive/reactive compounds that become conductive in response to exposure to differing components of the fluid.

3. The fluid sensor of claim 1, wherein fluid in the one or more windows can produce an electrical short across two or more turns of the inductor coil.

4. A method using the fluid sensor of claim 1, comprising detecting exposure to a fluid by measuring the change in resonant frequency of the tuned RLC during exposure to an electrically conductive fluid though the window in the film.

5. A fluid sensor comprising:
   a substrate; and
   a tuned RLC circuit configured on the substrate, the tuned RLC circuit including an inductor coil and a capacitor coupled through said substrate, and
   a film configured to limit exposure of the inductor coil to fluid, the film having one or more windows positioned such that fluid exposure is defined by the one or more windows, wherein fluid introduced through the one or more windows can cause a short in the RLC circuit;
   wherein exposure to a fluid causes a change in impedance of the RLC circuit before and after exposure to an electrically conductive fluid;
   wherein the one or more windows in the film is covered with a material that becomes conductive upon exposure to a fluid containing a specific component or class of components and;
   wherein there are multiple windows at least two of which are independently covered with differing receptive/reactive compounds that become conductive in response to exposure to differing components of the fluid.

6. The fluid sensor of claim 1, wherein the fluid sensor is initially tuned to a frequency between 6 MHz and 25 MHz.

7. The fluid sensor of claim 1, wherein the window is positioned such that the fluid exposure causes a predictable change in resonant frequency of the circuit.

8. A fluid sensor comprising:
   a substrate; and
   a tuned RLC circuit configured on the substrate, the tuned RLC circuit including an inductor coil and a capacitor coupled through said substrate, and
   a film configured to limit exposure of the inductor coil to fluid, the film having one or more windows positioned such that fluid exposure is defined by the one or more windows, wherein fluid introduced through the one or more windows can cause a short in the RLC circuit;
   wherein the window is positioned such that the fluid exposure causes a predictable change in electrical impedance of the circuit;
   wherein the one or more windows in the film is covered with a material that becomes conductive upon exposure to a fluid containing a specific component or class of components and;
   wherein there are multiple windows at least two of which are independently covered with differing receptive/reactive compounds that become conductive in response to exposure to differing components of the fluid.

9. The fluid sensor of claim 1, wherein the window is outside of the area of the inductive coil.

10. A fluid sensor comprising:

a substrate; and a tuned RLC circuit configured on the substrate, the tuned RLC circuit including an inductor coil and a capacitor coupled through said substrate, and a film configured to limit exposure of the inductor coil to fluid, the film having one or more windows positioned such that fluid exposure is defined by the one or more windows, wherein fluid introduced through the one or more windows can cause a short in the RLC circuit;

wherein an exposure to an electrically conductive fluid causes a shift in resonant frequency through a change in capacitance of the circuit;

wherein the one or more windows in the film is covered with a material that becomes conductive upon exposure to a fluid containing a specific component or class of components and; wherein there are multiple windows at least two of which are independently covered with differing receptive/reactive compounds that become conductive in response to exposure to differing components of the fluid.

11. A fluid sensor comprising:

a substrate; and a tuned RLC circuit configured on the substrate, the tuned RLC circuit including an inductor coil and a capacitor coupled through said substrate, and a film configured to limit exposure of the inductor coil to fluid, the film having one or more windows positioned such that fluid exposure is defined by the one or more windows, wherein fluid introduced through the one or more windows can cause a short in the RLC circuit;

wherein an exposure to an electrically conductive fluid causes a shift in resonant frequency through a change in resistance of the circuit;

wherein the one or more windows in the film is covered with a material that becomes conductive upon exposure to a fluid containing a specific component or class of components and;

wherein there are multiple windows at least two of which are independently covered with differing receptive/reactive compounds that become conductive in response to exposure to differing components of the fluid.

12. The fluid sensor of claim 1, wherein the sensor is coupled to an active, dedicated monitoring unit which provides data to a control/host information network on demand.

13. A fluid sensor comprising:

a substrate; and a tuned RLC circuit configured on the substrate, the tuned RLC circuit including an inductor coil and a capacitor coupled through said substrate, and a film configured to limit exposure of the inductor coil to fluid, the film having one or more windows positioned such that fluid exposure is defined by the one or more windows, wherein fluid introduced through the one or more windows can cause a short in the RLC circuit;

wherein the substrate is non-porous;

wherein the one or more windows in the film is covered with a material that becomes conductive upon exposure to a fluid containing a specific component or class of components and;

wherein there are multiple windows at least two of which are independently covered with differing receptive/reactive compounds that become conductive in response to exposure to differing components of the fluid.

14. A sensor comprising:

a substrate; and a tuned RLC circuit configured on the substrate, the tuned RLC circuit including an inductor coil and a capacitor coupled through said substrate, and a film configured to limit exposure of the inductor coil to an environmental element, the film having one or more windows positioned such that environmental exposure is defined by the one or more windows, wherein an environmental element introduced through the one or more windows can cause a short in the RLC circuit so that the RLC circuit responds at a different frequency after the environmental element is introduced;

wherein the one or more windows in the film is covered with a material that becomes conductive upon exposure to a fluid containing a specific component or class of components and;

wherein there are multiple windows at least two of which are independently covered with differing receptive/reactive compounds that become conductive in response to exposure to differing components of the fluid.

15. The sensor of claim 14, wherein the environmental element is a fluid.

16. The sensor of claim 15 wherein the fluid is a conductive fluid.

17. The sensor of claim 15 wherein the environmental element reacts with material in the window to produce the short.

18. The fluid sensor of claims 1, wherein the fluid sensor can be used in a three state system where the fluid sensor in the presence of fluid has a different response characteristic from fluid sensor absent the fluid.

* * * * *